US008654923B2

(12) United States Patent
Luan et al.

(10) Patent No.: US 8,654,923 B2
(45) Date of Patent: Feb. 18, 2014

(54) SYSTEM AND METHODS FOR USING A DYNAMIC SCHEME FOR RADIOSURGERY

(75) Inventors: Shuang Luan, Albuquerque, NM (US); Nathan Swanson, Albuquerque, NM (US); Lijun Ma, Foster City, CA (US)

(73) Assignee: STC.UNM, Albuquerque, NM (US)

( * ) Notice: Subject to any disclaimer, the term of this patent is extended or adjusted under 35 U.S.C. 154(b) by 416 days.

(21) Appl. No.: 12/990,338

(22) PCT Filed: May 4, 2009

(86) PCT No.: PCT/US2009/002733
§ 371 (c)(1),
(2), (4) Date: Mar. 17, 2011

(87) PCT Pub. No.: WO2009/137010
PCT Pub. Date: Nov. 12, 2009

(65) Prior Publication Data
US 2011/0160513 A1 Jun. 30, 2011

Related U.S. Application Data

(60) Provisional application No. 61/126,472, filed on May 4, 2008, provisional application No. 61/201,929, filed on Dec. 16, 2008.

(51) Int. Cl.
*A61N 5/10* (2006.01)
(52) U.S. Cl.
USPC .................................... 378/65; 600/1

(58) Field of Classification Search
USPC .................................... 378/65; 600/1
See application file for complete search history.

(56) References Cited

U.S. PATENT DOCUMENTS

| 5,373,844 | A | * | 12/1994 | Smith et al. | 600/427 |
| 6,385,477 | B1 | * | 5/2002 | Werner et al. | 600/407 |
| 6,449,336 | B2 | * | 9/2002 | Kim et al. | 378/65 |
| 2005/0096515 | A1 | * | 5/2005 | Geng | 600/315 |
| 2007/0286343 | A1 | * | 12/2007 | Maciunas et al. | 378/65 |

OTHER PUBLICATIONS

X.Hu et al., "A new Gamma Knife® radiosurgery paradigm: Tomosurgery", Medical Physics, vol. 34, No. 5, May 2007, pp. 1743-1758.

* cited by examiner

Primary Examiner — Hoon Song
Assistant Examiner — Danielle Fox
(74) Attorney, Agent, or Firm — Valauskas Corder LLC

(57) ABSTRACT

The present invention is a method and system for developing a dynamic scheme for Gamma Knife radiosurgery based on the concept of "dose-painting" to take advantage of robotic patient positioning systems on the Gamma Knife C and Perfexion units. The spherical high dose volume created by the Gamma Knife unit will be viewed as a 3D spherical "paintbrush", and treatment planning is reduced to finding the best route of this "paintbrush" to "paint" a 3D tumor volume. Under the dose-painting concept, Gamma Knife radiosurgery becomes dynamic, where the patient is moving continuously under the robotic positioning system.

27 Claims, 11 Drawing Sheets

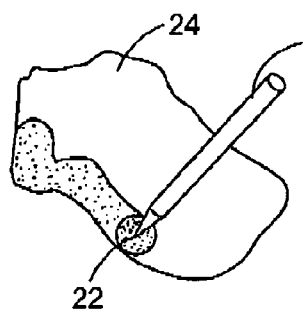
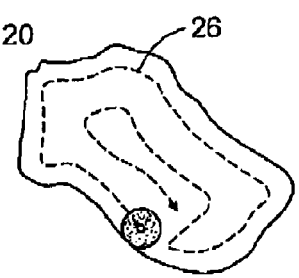
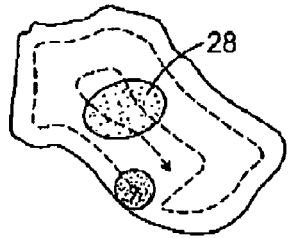
FIG. 1A  FIG. 1B  FIG. 1C
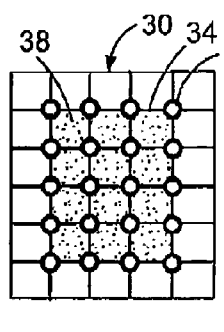
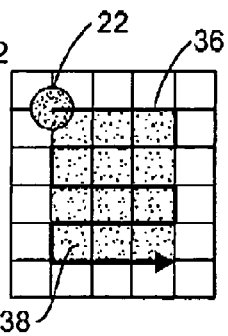
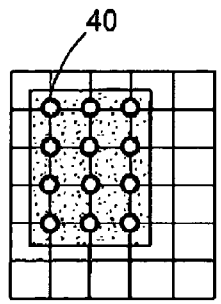
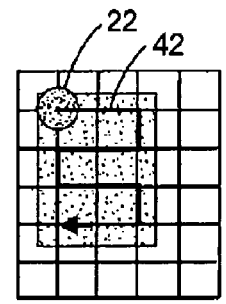
FIG. 2A  FIG. 2B  FIG. 2C  FIG. 2D
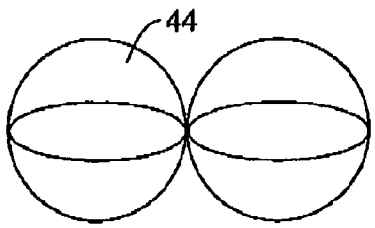
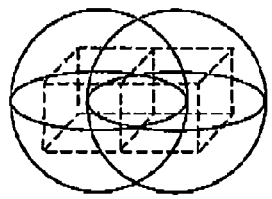
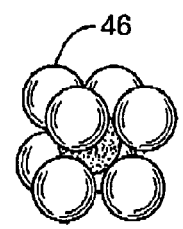
FIG. 3A  FIG. 3B  FIG. 3C

SYSTEM AND METHODS FOR USING A DYNAMIC SCHEME FOR RADIOSURGERY

This invention was made with government support under CBET-0755054 awarded by the National Science Foundation. The government has certain rights in the invention.

FIELD OF THE INVENTION

The invention relates generally to using a Gamma Knife for radiosurgery, and particularly to systems and methods for developing a dynamic scheme for Gamma Knife radiosurgery based on the concept of "dose-painting" to take advantage of Gamma Knife systems equipped with robotic patient positioning system (e.g., the Elekta® Gamma Knife Perfexion™ units). In the present invention, the spherical high dose volume created by the Gamma Knife unit will be viewed as a 3D spherical "paintbrush", and treatment planning reduces to finding the best route of this "paintbrush" to "paint" a 3D tumor volume. As such, Gamma Knife radiosurgery becomes a dynamic method, where the patient is moving continuously under the robotic positioning system.

BACKGROUND OF THE INVENTION

Gamma Knife radiosurgery has long been the treatment of choice for many brain tumors and functional disorders. According to Leksell Society treatment statistics, in 2006 alone a total of 57,768 patients received Gamma Knife radiosurgery for brain tumors and functional disorders.

In a Gamma Knife radiosurgery, γ-rays emitted from radioactive sources are used to eradicate tumors. These sources are placed in a hemispherical, linear, or circular array and their γ-ray beams are focused to a single point, creating a spherical high dose volume. Current Gamma Knife systems can produce spherical high dose volumes of different sizes by either external beam collimators (e.g., the patient's helmet system in the Gamma Knife® C™ System) or automatic built-in beam collimators (e.g., in the Gamma Knife® Perfexion™ system).

In practice, Gamma Knife radiosurgery consists of a planning phase and a delivery phase. In the planning phase, a ball-packing approach is used for planning Gamma Knife treatment, whose goal is to "pack" the different sized spherical high-dose volumes (called "shots") into the target tumor volume to create a conformal radiation dose distribution. Thus, a Gamma Knife radiosurgery plan is basically a set of planned shots whose locations, sizes and beam-on times are determined.

In the delivery phase, a Gamma Knife treatment plan is delivered in a "step-and-shoot" manner. A Gamma Knife head frame will be surgically attached to the patient's skull to establish a reference coordinate system. For each planned shot, the patient is first positioned with respect to the attached head frame before being moved into the source housing unit to receive the shot. Since repositioning is an off-line procedure (i.e., performed when the patient is outside the source housing unit and not being exposed to radiation), a Gamma Knife treatment can be very time consuming.

Besides prolonged treatment times, current ball-packing based Gamma Knife treatment also has more serious drawbacks. Packing is a venerable topic in mathematics. Most packing problems exhibit substantial difficulty. Even restricted 2D versions have been proved to be computational intractable and have significant high time complexity. So far, there is no computer-based automatic commercial planning system for Gamma Knife radiosurgery.

Instead, Gamma Knife treatments are mostly planned by humans through trial-and-error. Since the planner has to adjust many parameters (such as the number of shots, the locations, beam-on times and sizes of the shots) in a complex 3D anatomy, it is difficult and time-consuming to develop a high quality treatment plan. As a result, current Gamma Knife treatment can only prescribe a single isodose line (40-50% of the maximum dose) to cover the peripheral of the target tumor volume and leaves high dose spot randomly scattered inside the target. This inability to prescribe multiple isodose distributions limit the applications of functional imaging techniques such as magnetic resonance spectroscopy (MRS), which can reveal high tumor burden regions that require dose escalations to sub-regions inside the targeted tumor with multiple isodose distributions.

Accordingly, it would be advantageous to develop a dynamic scheme for Gamma Knife radiosurgery based on the concept of "dose-painting" to take advantage of robotic patient positioning system on the Gamma Knife C and Perfexion units.

It would be advantageous to develop a dynamic scheme for Gamma Knife radiosurgery in which the spherical high dose volume created by the Gamma Knife unit will be viewed as a 3D spherical "paintbrush".

It would also be advantageous to develop a dynamic scheme for Gamma Knife radiosurgery in which the treatment planning reduces to finding the best route of this "paintbrush" to "paint" a 3D tumor volume.

It would also be advantageous to develop a dynamic scheme for Gamma Knife radiosurgery in which the patient is moving continuously under the robotic positioning system.

SUMMARY OF THE INVENTION

The present invention is a method and system for a dynamic scheme for Gamma Knife radiosurgery which will overcome the drawbacks of current step-and-shoot scheme. The present invention is based on the concept of "dose-painting" and is designed to take advantage of the robotic patient positioning system on the Gamma Knife units.

In the present invention, the spherical high dose volume created by the Gamma Knife unit is viewed as a 3D spherical "paintbrush", and treatment planning reduces to finding the best route of the "paintbrush" to "paint" a 3D tumor volume. Under this dose-painting concept, a Gamma Knife radiosurgery plan would be a 3D route of the beam source and the delivery would become dynamic, where the patient is moving continuously under the robotic positioning system. Because of the relatively low dose rate, the motions of the patient are very smooth and the treatment procedure is very comfortable. With the introduction of the helmet-free Gamma Knife systems such as the Elekta® Perfexion™ system, collision is much less of concern.

As compared with the current step-and-shoot Gamma Knife approach, the scheme of the present invention has the following advantages: (1) It is easier to develop a fully automatic turn-key solution to Gamma Knife radiosurgery planning (described in more detail herein is the full automatic inverse planning algorithm for dynamic Gamma Knife radiosurgery); (2) the present invention can deliver much more conformal dose distribution to the targeted tumor because of its continuous motions; (3) the present invention will significantly shorten treatment times by eliminating most of the off-line repositioning; (4) the present invention can allow for elaborate plans with multiple isodose distributions (note that to increase the dose in certain sub-regions in dynamic Gamma Knife radiosurgery, one only needs to "slow down" the speed of the source when it passes through the region; and (5) Combining the present invention with the design of the latest the Gamma Knife® Perfexion™ system, it may be possible to extend Gamma Knife radiosurgery to other anatomical sites such as C-spine lesion Gamma Knife radiosurgery.

The present invention is further based on the development of a fully automatic inverse planning system for dynamic Gamma Knife radiosurgery, in which the core of the planning system is an optimization module. This planning algorithm as more fully described herein mainly includes the following steps:

1) A large set S of potential shots is generated based on the available amount of memory by a hybrid approach that uses both deterministic and randomized shot selection methods.

2) An optimization is performed on S and selects a subset S* of shots.

3) A traveling salesman tour is calculated for the shot locations in S* and is used as the final radiosurgery plan.

4) A final dose calculation is performed on the final route using fine interpolations.

Accordingly, it is an object of the present invention to develop a dynamic scheme for Gamma Knife radiosurgery based on the concept of "dose-painting" to take advantage of robotic patient positioning system on the latest Gamma Knife units.

It is an object of the present invention to develop a dynamic scheme for Gamma Knife radiosurgery in which the spherical high dose volume created by the Gamma Knife unit will be viewed as a 3D spherical "paintbrush", and treatment planning reduces to finding the best route of this "paintbrush" to "paint" a 3D tumor volume.

It is another object of the present invention to develop a dynamic scheme for Gamma Knife radiosurgery in which the patient is moving continuously under the robotic positioning system.

It is another object of the present invention to develop a dynamic Gamma Knife radiosurgery that produces more uniform and more conformal plans.

It is another object of the present invention to develop a dynamic Gamma Knife radiosurgery that can increase the dose gradient between target and the surrounding critical structures.

It is another object of the present invention to develop a treatment planning of dynamic Gamma Knife radiosurgery which is fully automatic and a turn-key solution to Gamma Knife radiosurgery.

It is another object of the present invention to develop a dynamic Gamma Knife radiosurgery in which the tradeoff between delivery time and treatment quality can be calculated, giving the clinicians additional flexibility in deciding on the treatment plan.

It is another object of the present invention to develop a dynamic Gamma Knife radiosurgery that can be extended to anatomical sites outside the skull.

The described embodiments are to be considered in all respects only as illustrative and not restrictive, and the scope of the invention is not limited to the foregoing description. Those of skill in the art will recognize changes, substitutions and other modifications that will nonetheless come within the scope of the invention and range of the claims.

DETAILED DESCRIPTION OF THE DRAWINGS

While the present invention is described herein with relation to certain embodiments and applications, those with skill in this art will recognize changes, modifications, alterations and the like which still come within the spirit of the inventive concept, and such are intended to be included within the scope of the invention as expressed herein and as disclosed in the following drawings, description and claims.

FIGS. 1A through 1C are schematic illustrations of the dynamic Gamma Knife radiosurgery in accordance with the preferred embodiment;

FIGS. 2A through 2D are illustrations of the grid shifting function of the dynamic Gamma Knife radiosurgery in accordance with the preferred embodiment;

FIGS. 3A through 3C are illustrations of the 3-D lattice structure using shot selection in accordance with the preferred embodiment;

DETAILED DESCRIPTION OF THE PREFERRED EMBODIMENT

Figure 4:
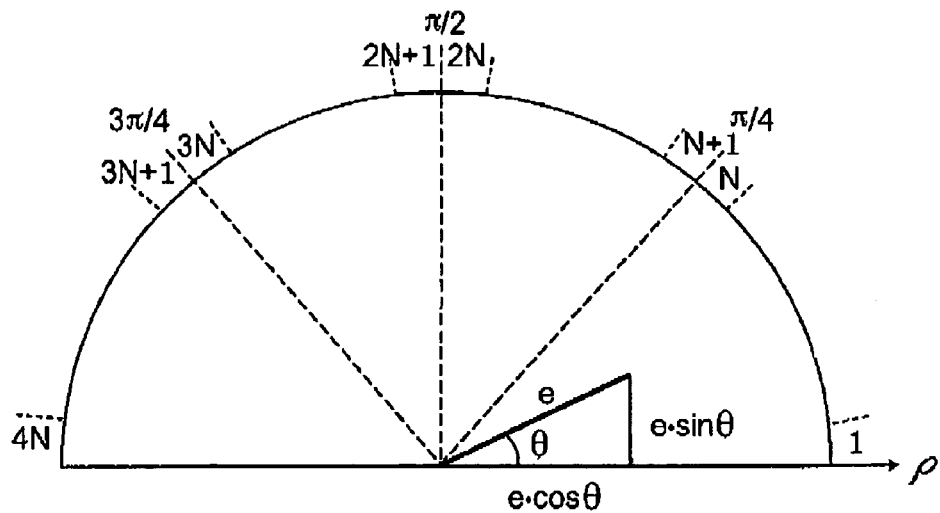
FIG. 4 is a depiction of a grid in accordance with the preferred embodiment divided with angular partitions.

As described herein, the Gamma Knife has been the treatment of choice for various brain tumors and functional disorders. Current Gamma Knife radiosurgery is planned in a "ball-packing" approach and delivered in a "step-and-shoot" manner, i.e., it aims to "pack" the different sized spherical high-dose volumes (called "shots") into a tumor volume.

The present invention is a dynamic scheme for Gamma Knife radiosurgery based on the concept of "dose-painting" to take advantage of the new robotic patient positioning system on the latest Gamma Knifes systems, such as the Elekta® C™ and Perfexion™ units. In the scheme of the present invention, the spherical high dose volume created by the Gamma Knife unit will be viewed as a 3D spherical "paintbrush", and treatment planning reduces to finding the best route of this "paintbrush" to "paint" a 3D tumor volume.

Under the dose-painting concept of the present invention, Gamma Knife radiosurgery becomes dynamic, where the patient is moving continuously under the robotic positioning system.

Implemented as part of the present system and methods is a fully automatic dynamic Gamma Knife radiosurgery treatment planning system, where the inverse planning problem is solved as a traveling salesman problem combined with constrained least square optimizations. Experimental studies of dynamic Gamma Knife radiosurgery indicate that (1) dynamic Gamma Knife radiosurgery is ideally suited for fully automatic inverse planning, where high quality radiosurgery plans can be obtained in minutes of computation; (2) dynamic radiosurgery plans are more conformal than step and shoot plans and can maintain steep dose gradient (around 13% per mm) between the target tumor volume and the surrounding critical structures; (3) it is possible to prescribe multiple isodose lines with dynamic Gamma Knife radiosurgery, so that the treatment can cover the periphery of the target volume while escalating the dose for high tumor burden regions; and (4) with dynamic Gamma Knife radiosurgery, one can obtain a family of plans representing a tradeoff between the delivery time and the dose distributions, thus giving the clinician one more dimension of flexibility of choosing a plan based on the clinical situations.

In a Gamma Knife radiosurgery, γ-rays emitted from radioactive cobalt-60 sources are used to eradicate tumors. These sources are placed in a hemispherical, circular or linear array and their Y-ray beams are focused to a single point, creating a spherical high dose volume. Current Gamma Knife systems can produce spherical high dose volumes of different sizes by either external beam collimators (e.g., the patient's helmet system in the Gamma Knife® C™ System) or automatic built-in beam collimators (e.g., in the Gamma Knife® Perflexion™ system).

In practice, Gamma Knife radiosurgery consists of a planning phase and a delivery phase. In the planning phase, a ball-packing approach is used for planning Gamma Knife treatment, whose goal is to "pack" the different sized spherical high-dose volumes (called "shots") into the target tumor volume to create a conformal radiation dose distribution. Hence, a Gamma Knife radiosurgery plan is basically a set of planned shots whose locations, sizes and beam-on times are determined. In the delivery phase, a Gamma Knife treatment plan is delivered in a "step-and-shoot" manner. A Gamma Knife head frame is surgically attached to the patient's skull to establish a reference coordinate system. For each planned shot, the patient is first positioned with respect to the attached head frame before being moved into the source housing unit to receive the shot. Since repositioning is an off-line procedure (i.e., performed when the patient is outside the source housing unit or the sources have been retracted to avoid radiation exposure), a Gamma Knife treatment can be very time consuming.

Besides prolonged treatment times, current ball-packing based Gamma Knife treatment also have more serious drawbacks. Most packing problems exhibit substantial difficulty. Even restricted 2D versions have been proved to be computationally intractable and have significant high time requirement. So far, there is no computer-based automatic commercial planning system for Gamma Knife radiosurgery. As a result, Gamma Knife treatments are mostly planned by humans through trial-and-error. Since the planner has to adjust many parameters (such as the number of shots, the locations, beam-on times and sizes of the shots) in a complex 3D anatomy, it is difficult and time-consuming to develop a high quality treatment plan. As a result, current Gamma Knife treatment can only prescribe a single isodose line (typically 40-50% of the maximum dose) to cover the periphery of the target tumor volume and leaves high dose region randomly scattered inside the target. This inability to prescribe multiple isodose distributions limits the applications of functional imaging techniques such as magnetic resonance spectroscopy (MRS), which can reveal high tumor burden regions where dose escalations to sub-regions inside the targeted tumor with multiple isodose distributions could be beneficial.

The present invention is a dynamic scheme for Gamma Knife radiosurgery, which overcomes the drawbacks of current step-and-shoot schemes. The systems and methods of the present invention are based on the concept of "dose-painting" and is designed to take advantage of the new robotic patient positioning system on the latest Gamma Knife units. In this system, the spherical high dose volume created by the Gamma Knife unit is viewed as a three-dimensional ("3D") spherical "paintbrush" and treatment planning reduces to finding the best route of the "paintbrush" to "paint" a 3D tumor volume.

FIGS. 1A and 1B show a schematic illustration of the dynamic Gamma Knife radiosurgery scheme in accordance with the present invention, in which the paintbrush 20 creates a high dose 22 over the course of the target volume 24 by following a path or "best route" 26. FIG. 1C shows how sub-region dose escalation 28, can be achieved by slowing down the speed of the paintbrush 20 over the path 26.

Under this dose-painting concept, a Gamma Knife radiosurgery plan would be a 3D route 26 of the beam source 20 and the delivery would become dynamic, where the patient (not shown) is moving continuously under the robotic positioning system. Because of the relatively low dose rate 22, the motions of the patient are very smooth and the treatment procedure is very comfortable. With the introduction of the helmet-free Gamma Knife systems such as the Elekta® Perfexion™ system, collision is much less of a concern.

Compared with the current step-and-shoot Gamma Knife approach, with the present invention (1) it is easier to develop a fully automatic turn-key solution to Gamma Knife radiosurgery planning (as described below in the fully automatic inverse planning algorithm for dynamic Gamma Knife radiosurgery); (2) it can deliver much more conformal dose distributions 22 to the targeted tumor 24 because of its continuous motions; (3) it will significantly shorten treatment times by eliminating most of the off-line repositioning; (4) it can facilitate planning with multiple isodose distributions, since to increase the dose 22 in certain sub-regions 28 in dynamic Gamma Knife radiosurgery, the speed of the source merely needs to be "slowed down" when passing through the region 28; (5) combining the dynamic scheme of the present invention with the design of the latest Gamma Knife® Perfexion™ system, it may be possible to extend Gamma Knife radiosurgery to other anatomical sites such as C-spine lesion Gamma Knife radiosurgery.

The systems and methods of the present invention contemplate a fully automatic inverse planning system for dynamic Gamma Knife radiosurgery. In the preferred embodiment, the core of the planning system is the optimization module. However, other algorithms may also work in conjunction with the Gamma knife and still come within the scope of the present invention.

The preferred embodiment for the planning algorithm is composed of the following key steps: First, a large set S of potential shots is generated based on the available amount of memory by a hybrid approach that uses both deterministic and randomized shot selection methods. Second, an optimization is performed on S and selects a subset S* of shots.

Next, a "traveling salesman" tour is calculated for the shot locations in S* and is used as the final radiosurgery plan. Then, a final dose calculation is performed on the final route using fine interpolations.

The inputs to the dynamic Gamma Knife planning module include: (1) contoured brain anatomy, (2) prescription for each contoured structure and their weighting just like in the planning of intensity-modulated radiation therapy, (3) desired delivery time T, (4) available system memory M in megabytes of data (typically for a laptop computer, M=2 GB, and (5) maximum motion speed $v_{max}$ of the patient positioning system (for current patient positioning system, $v_{max}$=1~2 mm/s).

As described above, the first step of planning dynamic Gamma Knife radiosurgery is to generate a set S of potential shots. Although the shot selection algorithm is illustrated in conjunction with the latest Perfexion™ system, the algorithm can also be adapted to any Gamma Knife systems equipped with a robotic patient positioning system.

Assuming that the dose grid used in planning takes m megabytes of memory storage. With M megabytes of total memory available, the maximum number of shots that the system can handle without I/O operations (i.e., everything is in memory) is $$n = \frac{M}{m}.$$

The latest Gamma Knife Perfexion system consists of 8 sectors of collimators; each sector can be configured to either close or produce shots of diameters 4 mm, 8 mm, and 16 mm. This yields a total of $4^8-1=2^{16}-1=65535$ possible multi-sector configurations each leading to a different spherical high dose volume (the −1 comes from when all sectors are closed). It is impossible both space-wise and time-wise to directly optimize all of these multi-sector configurations, and one way to overcome this is to optimize the individual-sector configurations. In particular, an individual sector configuration is obtained by opening one and only one sector in each shot. This gives 3×8 individual sector configurations.

In the preferred embodiment of the dynamic Gamma Knife radiosurgery planning system, for each potential shot location, 24 shots are introduce, one for each individual-sector configuration. An optimization is then made based on this collection of individual-sector shots. The multi-sector shots are obtained by combining individual sector shots after optimization. Thus the total number of shot locations is n/24.

Assuming that the target tumor volume is V, in the randomized shot selection process, n/24 points are chosen uniformly at random from this volume V.

In some situations, when the tumor is large, the constant multiplicative factor 1/24 may significantly reduce the potential locations where shots are placed. This can be dealt with either by using the deterministic shot selection method as described below, or for each shot location, a number of configurations can be chosen uniformly at random from the collection of the 24 individual-sector configurations plus the 4 mm, 8 mm, and 16 mm shots with all sectors open.

Experiments indicate that when the tumor is large, the available amount of memory in most desktop or laptop computers may not be enough to produce a high quality plan with randomized shot selections. In these situations, a deterministic shot selection algorithm can be used.

FIGS. 2A through 2D Illustrate the concept of grid shifting in two-dimensions ("2D"). FIG. 2A illustrates the imposition of a lattice 30 and determining the set of intersections S 32 on the underlying grid 34 that has to be traversed by the route 36 (FIG. 2B) to cover the tumor 38. FIG. 2B shows the traveling salesman tour of S 36 covering the targeted tumor 38. FIG. 2C shows that the number of intersections 40 that has to be traversed by the route 36 can be significantly reduced after grid shifting. FIG. 2D indicates that the length of the route 42 is reduced from 16 units in FIG. 2B to 9 units after grid shifting (a 44% reduction).

The deterministic shot selection algorithm includes the following steps: step 1 imposes a 3D lattice structure of size d to the given target volume 38 (see FIG. 2A) (The size d of the grid is calculated based on the size of the shots used as explained below). In step 2, the set of intersections S 32 on the underlying grid 34 that must be traversed by the shot 22 to cover the tumor 38 is determined. For this determination, any intersection of the grid 34 is included in S 32 if it is either inside or is within a distance d/2 to the target tumor volume V 38 (FIG. 2A illustrates S).

The third step applies 3D grid shifting and may also involve grid rotation, as described below, to minimize the set S 32 of intersections. When grid shifting is used, the quality and the length of the final route can both be significantly improved.

FIGS. 2C and 2D illustrate the motivation behind grid shifting. As can be seen from FIG. 2D, after shifting the underlying grid structure, the route of the shot 42 is shortened by about 44% and the conformity is also significantly improved. This improvement comes from the dramatic reduction in the number of intersections of S (as shown in FIG. 2C).

Steps (1)-(3) can be applied for 4 mm, 8 mm, and 16 mm shots with all sectors open. In FIG. 3A through 3C, each shot will be modeled as a sphere 44. Thus, if a 3D regular grid is used, the 3D grid must shrink as shown in FIGS. 3A and 3B in order to ensure coverage. Alternatively, we can also use the BCC (Body Centered Cubic) lattice shown in FIG. 3C 46, which exhibits a dense packing of the tumor volume.

Figure 5:
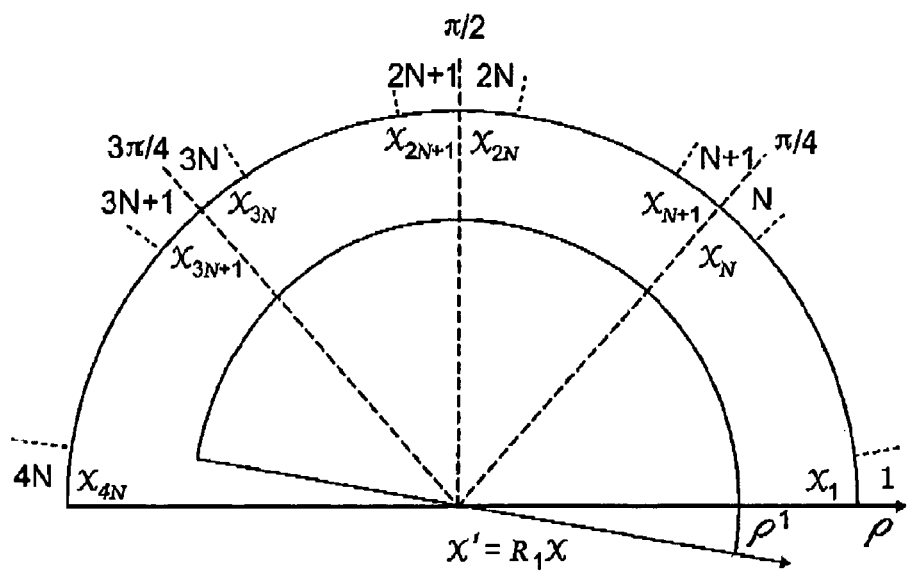
FIG. 5 is a depiction of a grid rotated in accordance with the preferred embodiment

A further reduction of the length of the final dynamic route and quality of the plan can be accomplished using a technique called grid rotation. FIGS. 4 and 5, which depict a grid, are used to illustrate grid rotation in 2D.

FIG. 4 shows the grid being divided into angular partitions. By increasing N, one can reduce the perturbation factor needed to align T to the grid. Allowing T to be an arbitrary tour of with unrestricted motions, and let |T| denote the length of the tour T. Now consider an edge e of T with a length of |e|. Let θ(e) be the angle between e and an underlying polar coordinate system (ρ,θ). One may view the direction of the vector ρ is aligned with x-axis of the underlying regular grid G that is about to be rotated. Since one can always choose to move either end of the edge e to the origin, it suffices for us to assume 0≤θ(e)≤π. If one perturbs e with respect to G, its length will become |e|·(|cos(θ(e))|+|sin(θ(e))|).

Assume a partitioning of the angular range [0,π] into 4N angular intervals. Let $I_i$ (i=1, . . . , 4N) to denote each angular interval with $$I_i = \left[\frac{\pi}{4N} \cdot i, \frac{\pi}{4N} \cdot (i+1)\right].$$

Consider the histogram of the edges of T with respect to these 4N angular intervals. Let $x_i$ denote the total length of those edges of T whose angle θ is in $I_i$. The function θ(θ)=|cos θ|+|sin θ| is increasing in the angular range $$\left[0, \frac{\pi}{4}\right]$$

and $$\left[\frac{3\pi}{4}, \pi\right]$$

and decreasing in the angular range $$\left[\frac{\pi}{4}, \frac{3\pi}{4}\right].$$

Thus, if one perturbs T, the increase due to perturbing the edges that constitutes $x_i$ is bounded by $$x_i \left( \left| \cos \frac{\pi}{4N} \cdot i \right| + \left| \sin \frac{\pi}{4N} \cdot i \right| \right)$$

if $1 \le i \le N$ and $3N+1 \le i \le 4N$, and is bounded by $$x_i \left( \left| \cos \frac{\pi}{4N} \cdot (i-1) \right| + \left| \sin \frac{\pi}{4N} \cdot (i-1) \right| \right) \text{ if } N+1 \le i \le 3N.$$

Thus, the new length of the perturbed Lawn Mowing tour T' will be bounded by:

$$\sum_{i=1}^{N} \left( \left| \cos\left(\frac{\pi}{4N} \cdot i\right) \right| + \left| \sin\left(\frac{\pi}{4N} \cdot i\right) \right| \right) \cdot x_i +$$

$$\sum_{i=N+1}^{2N} \left( \left| \cos\left(\frac{\pi}{4N} \cdot (i-1)\right) \right| + \left| \sin\left(\frac{\pi}{4N} \cdot (i-1)\right) \right| \right) \cdot x_i +$$

$$\sum_{i=2N+1}^{3N} \left( \left| \cos\left(\frac{\pi}{4N} \cdot (i-1)\right) \right| + \left| \sin\left(\frac{\pi}{4N} \cdot (i-1)\right) \right| \right) \cdot x_i +$$

$$\sum_{i=3N+1}^{4N} \left( \left| \cos\left(\frac{\pi}{4N} \cdot i\right) \right| + \left| \sin\left(\frac{\pi}{4N} \cdot i\right) \right| \right) \cdot x_i.$$

Now let $x=(x_1, \ldots, x_{4N})$ and $\mu=(\mu_1, \ldots, \mu_{4N})$, where $$\mu_i = \left| \cos\left(\frac{\pi}{4N} \cdot i\right) \right| + \left| \sin\left(\frac{\pi}{4N} \cdot i\right) \right|$$

if $1 \le i \le N$ and $3N+1 \le i \le 4N$, and $$\mu_i = \left| \cos\left(\frac{\pi}{4N} \cdot (i-1)\right) \right| + \left| \sin\left(\frac{\pi}{4N} \cdot (i-1)\right) \right| \text{ if } N+1 \le i \le 3N,$$

then $|T'| \le \langle x,\mu \rangle$, where $\langle , \rangle$ is the inner product operator. Refer to x as the frequency vector and $\mu$ as the perturbation vector. Note that $\Sigma_{i=1}^{4N} x_i = |T|$. Now consider rotating the grid clockwise by $\pi/4N \cdot k$. The edges that fall into $I_i$ will now fall into $I_{(i+k) \mod 4N}$. Thus, the new frequency vector is obtained by performing a cyclic shifting of x to the right by k positions. Let $R_k$ to denote the cyclic shifting operator of a vector to the right by k positions, and use $T_k$ to denote the perturbed tour when the grid is rotated clockwise by $\pi/4N \cdot k$, then the new frequency vector of $T_k$ is $R_k x$ with a length $$\Sigma_{k=1}^{4N} |T_k| = \Sigma_{k=1}^{4N} \langle R_k x, \mu \rangle = \Sigma_{k=1}^{4N} \Sigma_{i=1}^{4N} (R_k x)_i \cdot \mu_i = \Sigma_{i=1}^{4N} (\mu_i \Sigma_{k=1}^{4N} (R_k x)_i) = \Sigma_{i=1}^{4N} (\mu_i \Sigma_{k=1}^{4N} x_{i-k}) = \Sigma_{i=1}^{4N} \mu_i \Sigma_{i=1}^{4N} x_i = \Sigma_{i=1}^{4N} \mu_i \cdot |T|.$$

Since the average length of the 4N perturbed tour (i.e., $T_1, \ldots, T_{4N}$) is $|T| \cdot \Sigma_{i=1}^{4N} \mu_i / 4N$, at least one of the perturbed tours $T_k$ is $|T_k| \le |T| \cdot \Sigma_{i=1}^{4N} \mu_i / 4N$. As $N \to \infty$, $|T| \cdot \Sigma_{i=1}^{4N} \mu_i / 4N = \Sigma_{i=1}^{4N} \mu_i \cdot \pi 4N / \pi \approx \int_0^{\pi} (|\cos \theta| + |\sin \theta|) d\theta = 4/\pi \approx 1.273$. Further, one can bound the perturbation factor error for grid rotation to be $\pi/4 + \pi^2/16N$. To apply the above technique, one needs to partition the $[0,\pi]$ angular intervals and apply a grid shifting for each angular interval. For 3D situations, assuming a polar coordinate is used, i.e., $(\rho,\theta,\phi)$, one needs to partition $\theta, \phi$ and apply grid shifting for each angular interval pairs. The technique can also randomized by applying a random sample of the angles.

In the preferred embodiment, shot selection is determined by using a constrained least square optimization algorithm. Once a collection S of potential shots has been generated, a subset of shots S* such that $$\left\| \sum_{i \in S^*} t_i \dot{D}_i - D^* \right\|$$

is minimized, where $\dot{D}_i$ is the dose rate distribution for the $i^{th}$ shot, $t_i$ is the beam-on time for the $i^{th}$ shot, and D* is the ideal dose distribution from prescription. Minimizing the difference between the created dose distribution $$\sum_{i \in S^*} t_i \dot{D}_i$$

and the ideal dose distribution D*, ensures that the final plan is as close to the prescribed dose distribution D* as possible. Further, the beam-on time $t_i$ for the selected shot must also satisfy: (a) $t_i \ge \delta$ for some threshold S that is calculated based on the maximum motion speed $v_{max}$ of the patient positioning system and the contribution due to "transit dose" at any given point (i.e., the dose delivered when the sources move in and out of position); and (b)

$$\sum_{i \in S^*} t_i \le T.$$

T is the input parameter for desired delivery time, and thus ensuring that the final delivery time doesn't exceed the desired delivery time.

To find such a subset S*, iterative constrained least square optimization is used. Specifically, in each iterations, we will first minimize $$\left\| \sum_{i \in S} t_i \dot{D}_i - D^* \right\|,$$

subject to $t_i \ge 0$ and $$\sum_{i \in S} t_i \le T,$$

then we eliminate all shots whose beam-on times is less than the threshold δ.

The final route is calculated using the well-known traveling salesman approximation algorithms. The optimal set of intersections actually induces a graph, whose vertices are intersections and whose edges are introduced by the underlying grid. Since the plan is dynamic, in order to evaluate its true quality, a linear interpolation of the route with 1 mm spacing and sum up the dose distribution for each interpolation point.

Implementation of the above optimization module for dynamic Gamma Knife radiosurgery can be accomplished using the standard C programming language. The program is coded carefully enough so that it runs on Microsoft Windows, Mac OS X, and various versions of Linux. Initial experiments indicate that for brain tumors, the optimization takes minutes on a MacBookPro laptop computer equipped with an Intel Core 2 Dual Processor at 2.5 GHz and 4 GB of memory. One of the reasons for such short computation times is because the iterative constrained least square optimization described above typically converges in 2 iterations.

Also, due to Co decay, the dose rate used above must be adjusted on a daily basis. Alternatively, this can be resolved by increasing the treatment time accordingly on a daily basis.

Figure 6A:
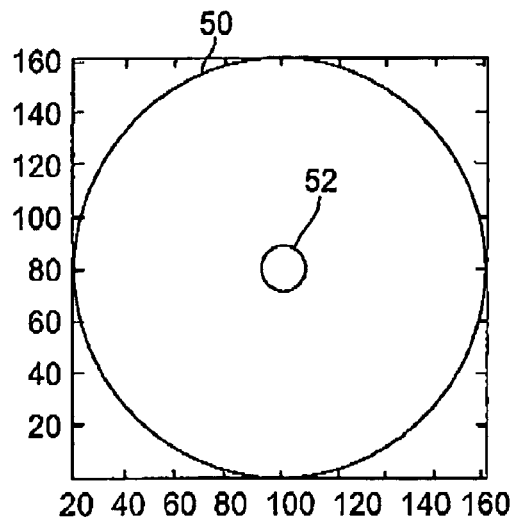
FIGS. 6A through 6C are schematic illustrations of the simulated phantoms containing tumors in accordance with the preferred embodiment.
Figure 6B:
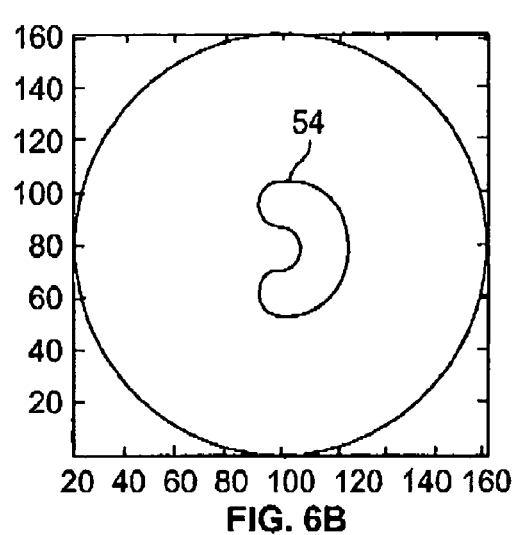
Figure 6C:
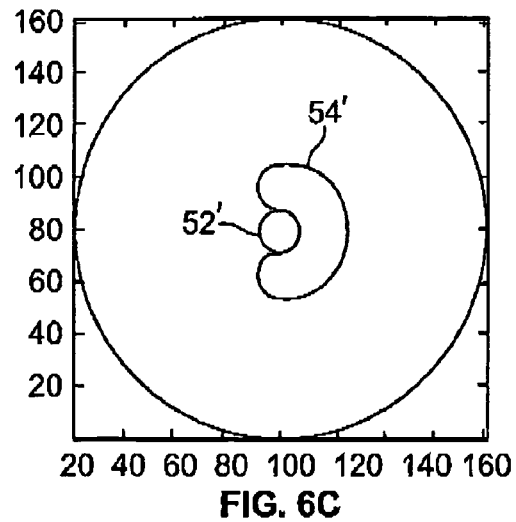

FIGS. 6A through 6C illustrate the results of experiments in accordance with the present invention with dynamic Gamma Knife radiosurgery using three simulated 3D phantoms. In all phantoms, the skull 50 is simulated with a sphere of radius 80 mm. FIG. 6A shows the first phantom, called a "ball phantom" which has a spherical tumor 52 of radius 10 mm. FIG. 6B show the second phantom, called a "C-shaped phantom" having a tumor of a C-shape 54. FIG. 6C shows the third phantom called the "combined phantom" which is obtained by combining the first and the second phantoms, where a spherically shaped critical structure 52' is surrounded a C-shaped tumor 54'.

FIGS. 7, 8 and 9 show the DVHs and the dose distributions of the dynamic Gamma Knife radiosurgery plans that are produced by the inverse planning system s described herein. As seen from these plots, dynamic Gamma Knife radiosurgery scheme are of a very high quality.

Figure 7A:
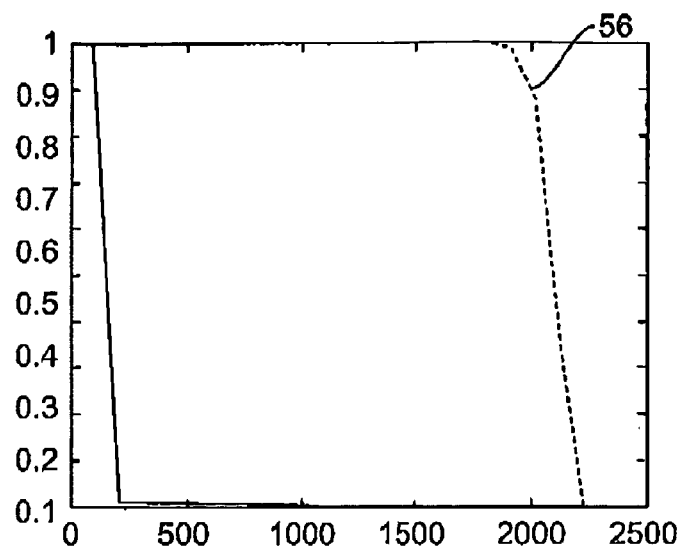
FIGS. 7A through 7C are schematic illustrations of the experimental results in accordance with the preferred embodiment.
Figure 7B:
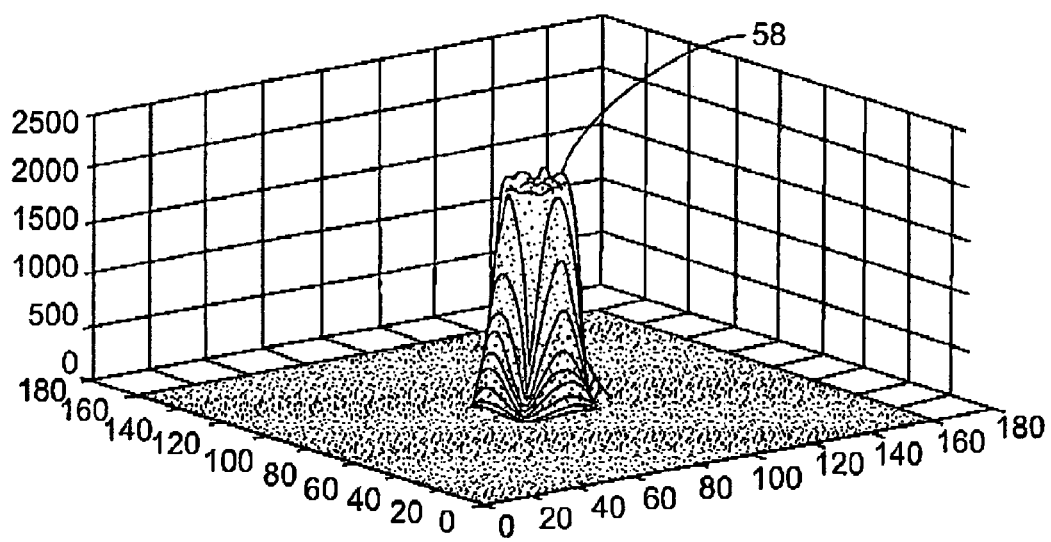
Figure 7C:
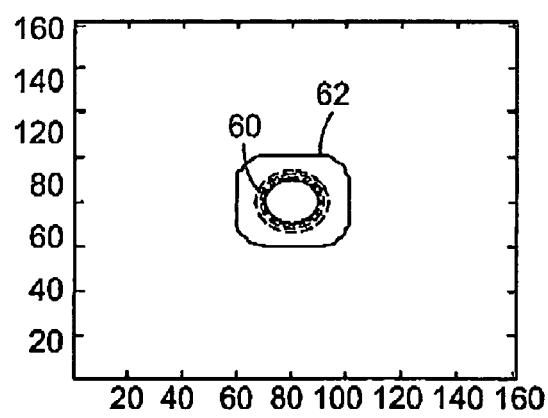

FIG. 7 shows the experimental results for the ball phantom 52 in accordance with FIG. 6A. FIG. 7A indicates the dose volume histogram 56. FIG. 7B shows the dose distributions 58, and FIG. 7C shows the Isodose distributions for the 90%, 80%, 70%, 60%, 50% and 40% isodose lines 60 (the outer boundary 62 is the dose grid used for optimization).

Figure 8A:
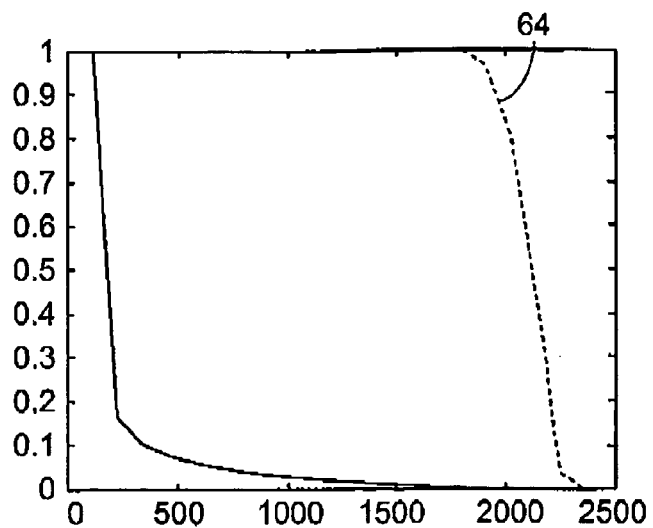
FIGS. 8A through 8C are schematic illustrations of the experimental results in accordance with the preferred embodiment.
Figure 8B:
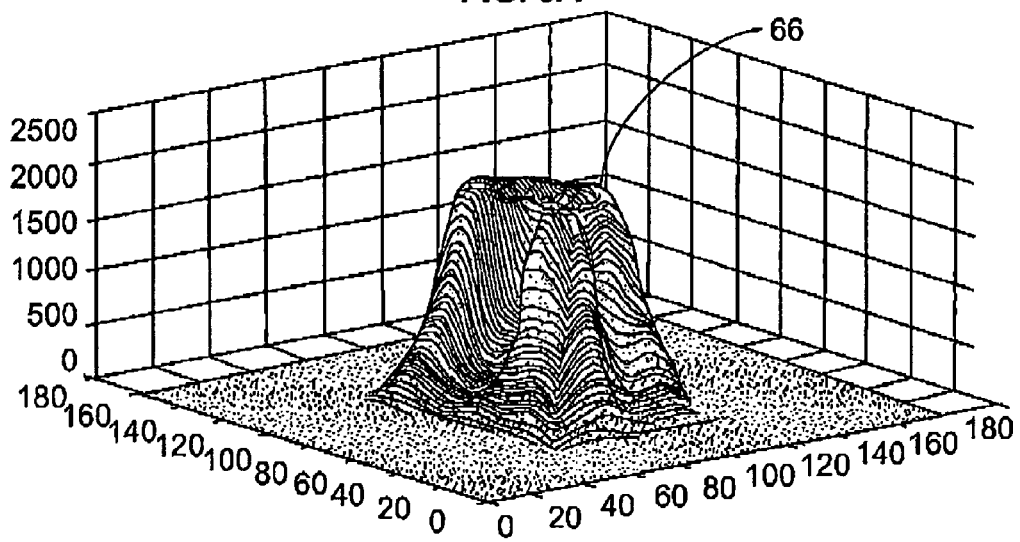
Figure 8C:
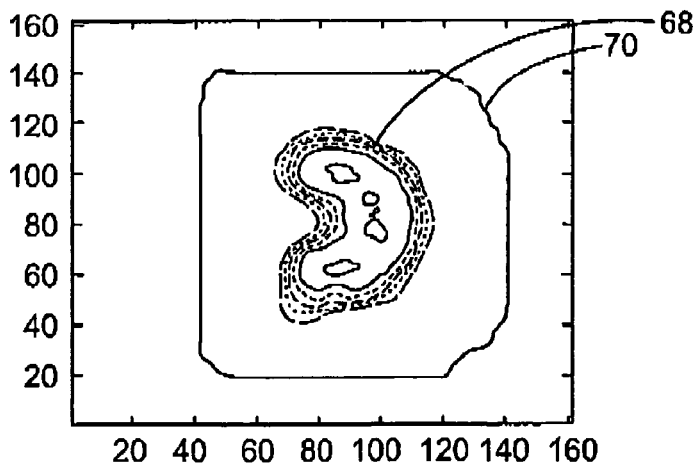

Likewise, FIG. 8 shows the experimental results for the C-shaped phantom 54 in accordance with FIG. 6B, including dose volume histogram 64 (FIG. 8A); dose distributions 66 (FIG. 8B) and Isodose distributions for the 90%, 80%, 70%, 60%, 50% and 40% isodose lines 68 (the outer boundary 70 is the dose grid used for optimization) (FIG. 8C).

Figure 9A:
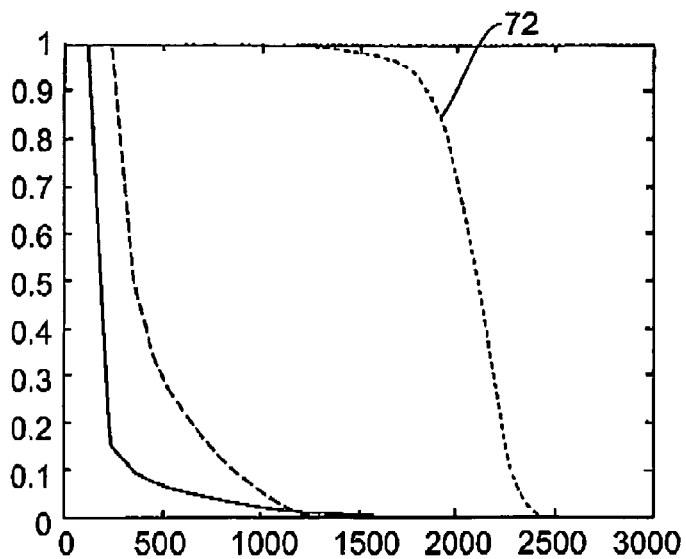
FIGS. 9A through 9C are schematic illustrations of the experimental results in accordance with the preferred embodiment.
Figure 9B:
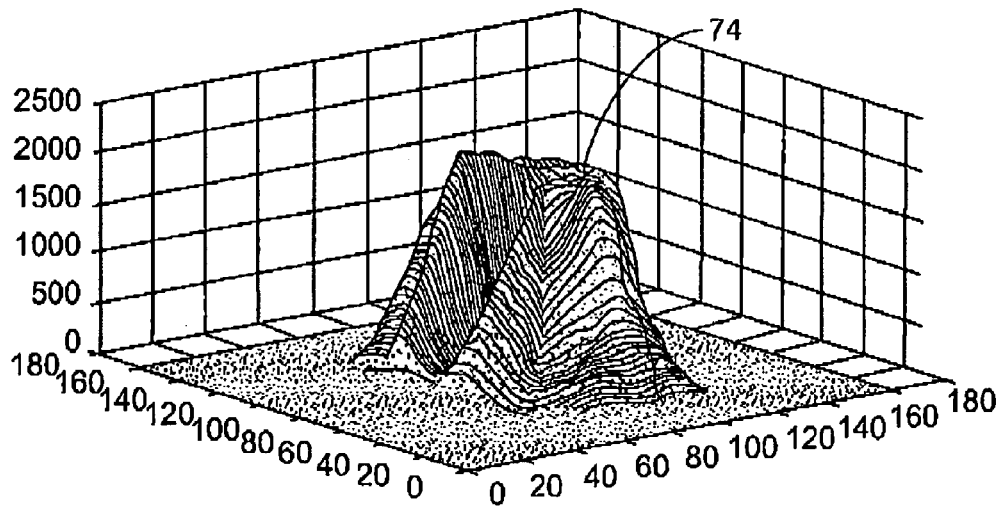
Figure 9C:
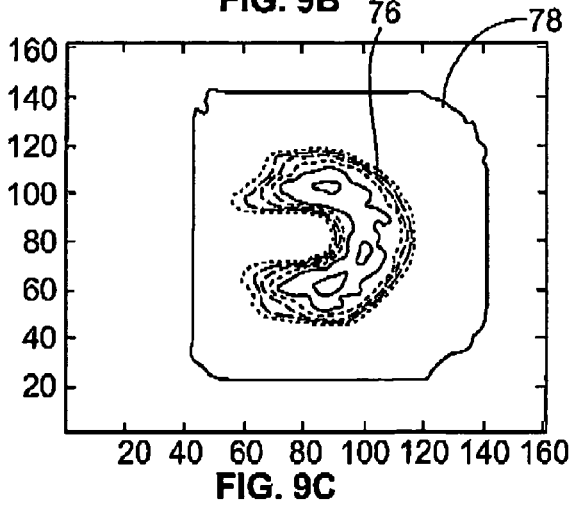

FIG. 9 also indicates experimental results, but for the combined phantom 52', 54'. FIG. 9A shows the dose volume histogram 72. FIG. 9B shows the dose distributions 74, and FIG. 9C shows the Isodose distributions for the 90%, 80%, 70%, 60%, 50% and 40% isodose lines 76 (the outer boundary 78 is the dose grid used for optimization).

Figure 10:
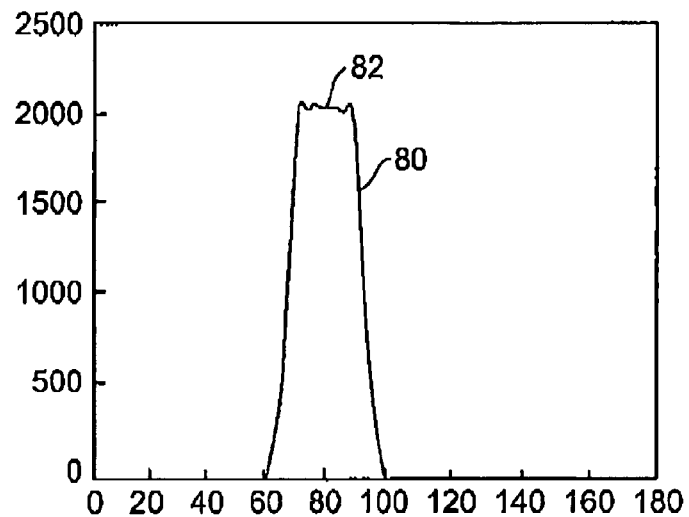
FIG. 10 is a graph of the dose profiles of the dynamic Gamma Knife radiosurgery plan in accordance with the preferred embodiment.

Another advantage of the dynamic Gamma Knife radiosurgery, is the ease at which uniform plans can be obtained due to the dynamic motion of the beam source. FIG. 10 shows the dose profiles 80 of the dynamic Gamma Knife radiosurgery plan of the ball phantom 52 (from FIG. 6A). It can be observed that the high dose region 82 is almost completely flat. It should be noted, however, that dose distributions of comparable uniformity are also achievable with conventional Gamma Knife treatment delivery if a single isocenter suffices to cover the target, as would likely be the case for the simple 2-cm diameter target studied here.

Figure 11:
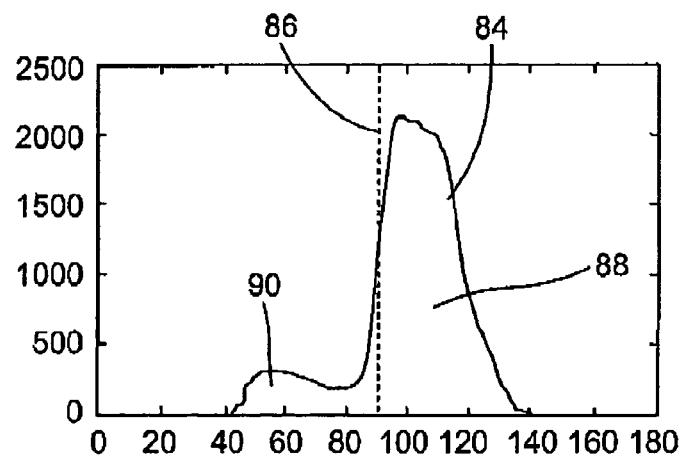
FIG. 11 is a graph of the dose profiles of the dynamic Gamma Knife radiosurgery plan in accordance with the preferred embodiment.

FIG. 11 shows the dose profile 84 of the combined phantom 52', 54' (from FIG. 6C), where the straight line 86 is the boundary between the tumor 88 to the right and the critical structure 90 to the left. With dynamic Gamma Knife radiosurgery in accordance with the present invention, the dose gradient between the target 88 and the adjacent structure 90 can be made more steep. Based on calculation, the dose gradient at the boundary is about 13% dose reduction per mm.

Yet another advantage of the dynamic Gamma Knife radiosurgery planning algorithm as set forth herein, is that given a delivery time T, it can calculate the plan with the optimal quality that can be delivered within T. One application of this feature is that a calculation can be made for a family of plans representing a tradeoff between delivery time and treatment quality.

Figure 12A:
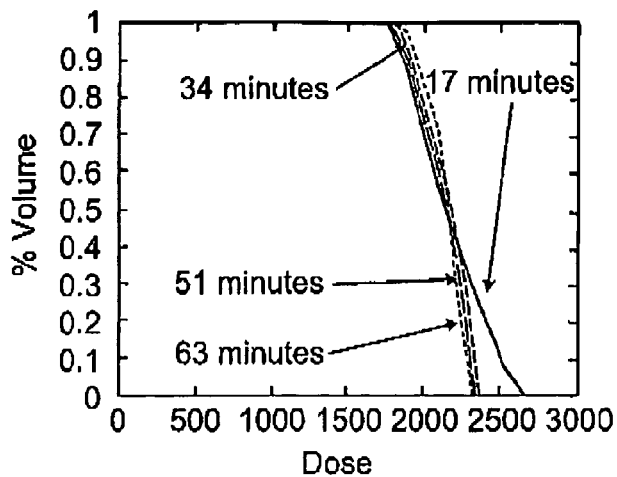
FIGS. 12A and 12B are timing graphs of the dynamic Gamma Knife radiosurgery plan in accordance with the preferred embodiment.
Figure 12B:
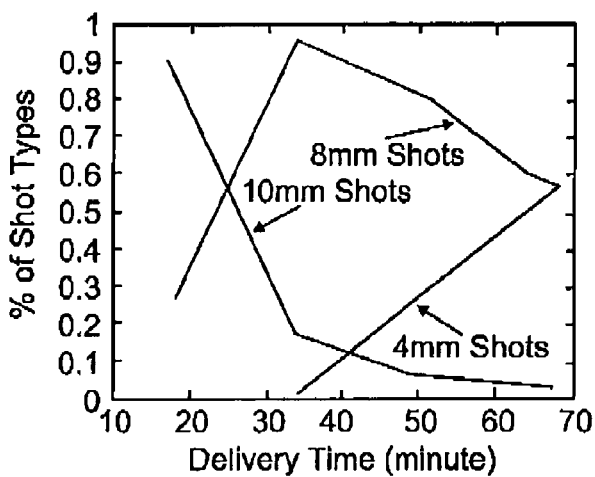

FIG. 12A shows such a tradeoff. As can be seen from the plot, as the delivery time increases, the uniformity and conformity of the plan improves. The reason for this is illustrated in FIG. 12B, which shows that as the delivery time increases, the planning system will initially try to switch from 16 mm shots to 8 mm shots, and then switch from 8 mm shots to 4 mm shots. Since the smaller the shots, the shaper the dose distribution, the plan quality improves. As the treatment time feature is that a calculation can be made for a family of plans representing a tradeoff between delivery time and treatment quality.

FIG. 12A shows such a tradeoff. As can be seen from the plot, as the delivery time increases, the uniformity and conformity of the plan improves. The reason for this is illustrated in FIG. 12B, which shows that as the delivery time increases, the planning system will initially try to switch from 16 mm shots to 8 mm shots, and then switch from 8 mm shots to 4 mm shots. Since the smaller the shots, the shaper the dose distribution, the plan quality improves. As the treatment time continue to increase, the planning system will eventually abandon all 16 mm and 8 mm shots in favor of the 4 mm shots. The ratio of 8 mm shots peaks when it can strike a balance between treatment time and treatment quality.

Alternatively, this tradeoff can be viewed in a way that for a fixed delivery time, the optimization will automatically select a shot distribution such that for large tumors, a higher ratio of larger shots such as 16 mm will be used, while for small tumors, a higher ratio of smaller shots such as 4 mm will be used. The ratio of 8 mm shot will peak for medium sized tumors, where it can strike a balance between tumor size and treatment time.

Figure 13:
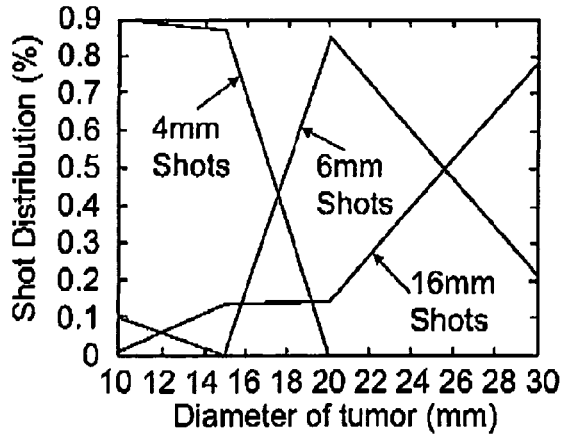
FIG. 13 is a timing graph of the dynamic Gamma Knife radiosurgery plan in accordance with the preferred embodiment.

This phenomenon is illustrated in FIG. 13, where the total delivery time is fixed at about half an hour, while the tumor size is increased from 10 mm to 30 mm in diameter.

Figure 14:
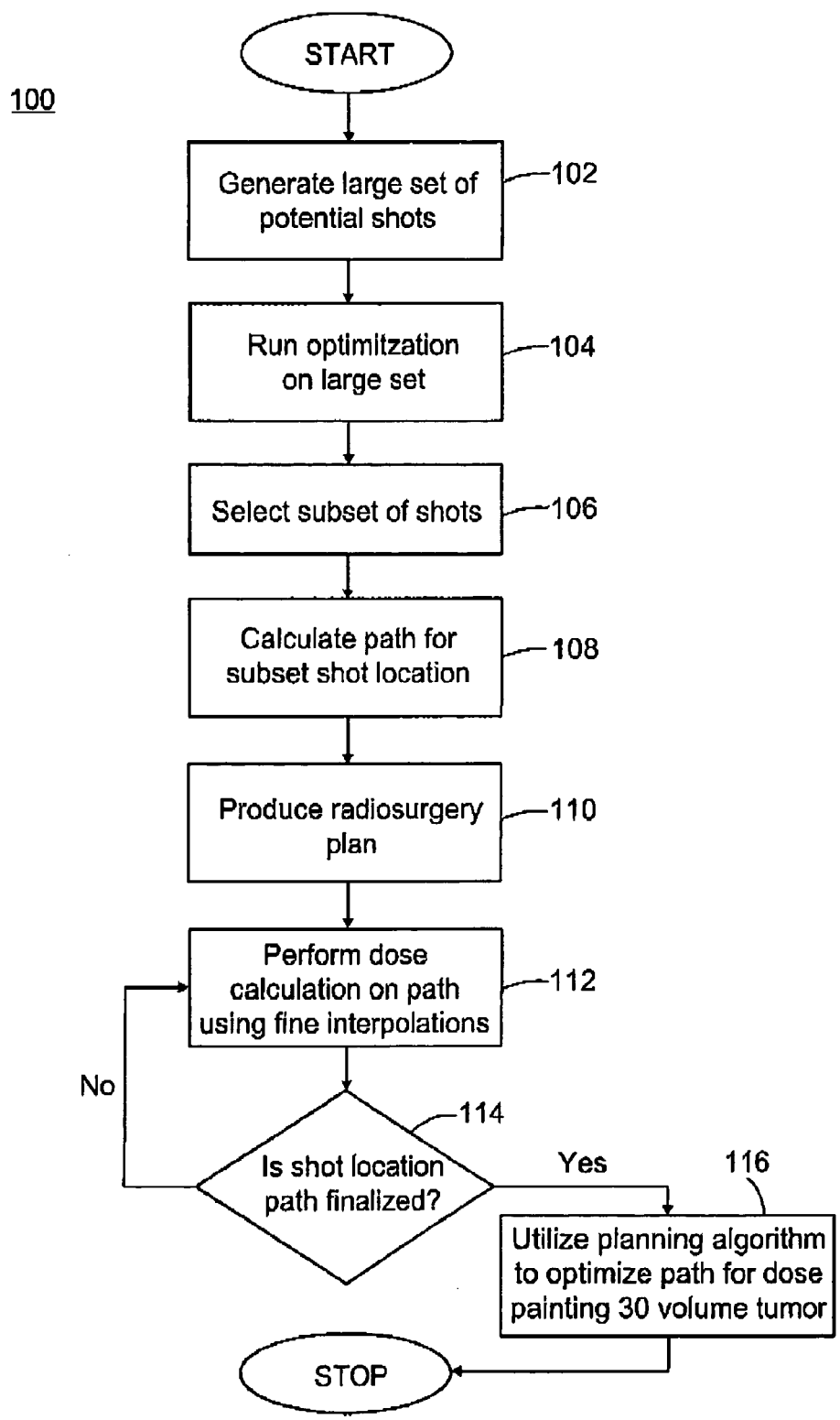
FIG. 14 is a flow chart of the method of the dynamic Gamma Knife radiosurgery in accordance with the present invention.

FIG. 14 illustrates a flow chart 100 in accordance with one embodiment of the present invention. As shown generally in FIG. 14, and described in detail herein, an initial set or large set S of potential dose-painting shots is generated at step 102 for use in the present invention. This large set S is generated based finalized, step 116 provides for a planning algorithm to be incorporated to optimize the path for dose-painting the 3D volume tumor using the Gamma Knife system.

Figure 15:
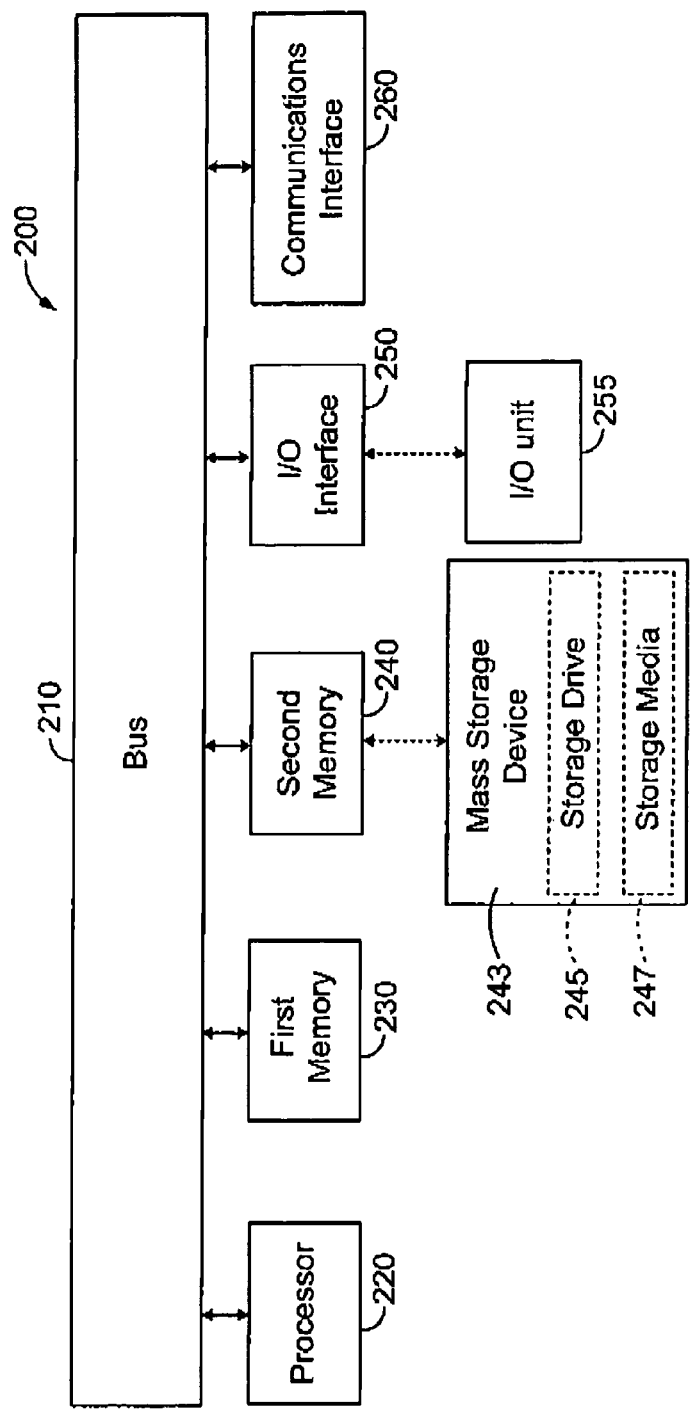
FIG. 15 is a system illustration of the method of the dynamic Gamma Knife radiosurgery in accordance with the present invention.

FIG. 15 illustrates an exemplary computer system 200, or network architecture, that may be used to implement the methods according to the present invention. One or more computer systems 200 may carry out the methods presented herein as computer code. One or more processors, such as processor 220, which may be a special purpose or a general-purpose processor is connected to a bus 210. Bus 210 can be used to connect the processor 220 to various other components of the system 200, but it is contemplated bus 210 may connect processor 220 to additional system components (not shown) such as the Gamma Knife described herein.

It is also contemplated that bus 210 can connect the processor 220 to other computer systems as necessary. Via the bus 210, the processor 220 can receive computer code. The term "computer code" includes, for example, programs, instructions, signals and/or data. The processor 220 executes computer code and may further send the computer code via the bus 210.

Computer system 200 may include one or more memories, such as first memory 230 and second memory 240. It is contemplated that the first memory 230, secondary memory 240, or a combination thereof function as a computer usable storage medium to store and/or access computer code. The first memory 230 and second memory 240 may be, for example, random access memory (RAM), read-only memory (ROM), a mass storage device, or any combination thereof.

As shown in FIG. 15, one embodiment of second memory 240 is a mass storage device 243, although it is contemplated that first memory 230 may be the mass storage device. The mass storage device 243 comprises a storage drive 245 and a storage media 247. It is contemplated that the storage media 247 may or may not be removable from the storage drive 245. Mass storage devices 243 with storage media 247 that are removable, otherwise referred to as removable storage media, allow computer code to be transferred to and/or from the computer system 200.

A mass storage device 243 may include, for example, a Compact Disc Read-Only Memory ("CDROM"), ZIP storage device, tape storage device, magnetic storage device, optical storage device, Micro-Electro-Mechanical Systems ("MEMS"), nanotechnological storage device, floppy storage device, hard disk device. Mass storage device 243 also includes program cartridges and cartridge interfaces (such as that found in video game devices), removable memory chips (such as an EPROM, or PROM) and associated sockets.

The computer system 200 may further or alternatively include other means for computer code to be loaded into or removed from the computer system 200, for example, input/output ("I/O") interface 250 and/or communications interface 260. Both the I/O interface 250 and the communications interface 260 allow computer code to be transferred between the computer system 200 and external devices including other computer systems. This transfer may be bi-directional or omni-direction to or from the computer system 200.

Computer code transferred by the I/O interface 250 and the communications interface 260 are typically in the form of signals, which may be electronic, electromagnetic, optical, or other signals capable of being sent and/or received by the interfaces. These signals may be transmitted via a variety of modes including, but not limited to, wire or cable, fiber optics, a phone line, a cellular phone link, infrared ("IR"), and radio frequency ("RE") link.

The I/O interface 250 may be any connection, wired or wireless, that allows the transfer of computer code. An I/O interface 250 includes, for example, an analog or digital audio connection, digital video interface ("DVI"), video graphics adapter ("VGA"), musical instrument digital interface ("MIDI"), parallel connection, PS/2 connection, serial connection, universal serial bus connection ("USB"), IEEE1394 connection, PCMCIA slot and card. In certain embodiments the I/O interface connects to an I/O unit 255, for example, a user interface, monitor, speaker, printer, touch screen display, etc.

The communications interface 260 is also any connection that allows the transfer of computer code. Communication interfaces include, but are not limited to, a modem, network interface (such as an Ethernet card), wired or wireless systems (such as Wi-Fi, Bluetooth, IR), local area networks, wide area networks, intranets, etc.

The invention is also directed to computer products, otherwise referred to as computer program products, to provide software that includes computer code to the computer system 200. Processor 220 executes the computer code in order to implement the methods of the present invention. As an example, the methods according to the present invention may be implemented using software that includes the computer code, wherein the software is loaded into the computer system 200 using a memory 230, 240 such as the mass storage drive 243, or through an I/O interface 250, communications interface 260, or any other interface with the computer system 200. The computer code in conjunction with the computer system 200 described herein may perform any one of, or any combination of, the steps of any of the methods presented herein. It is also contemplated that the methods according to the present invention may be performed automatically, or may be invoked by some form of manual intervention.

The computer system 200, or network architecture, of FIG. 15 is provided only for purposes of illustration, such that the present invention is not limited to this specific embodiment. It is appreciated that a person skilled in the relevant art knows how to program and implement the invention using any computer system or network architecture.

Figure 16A:
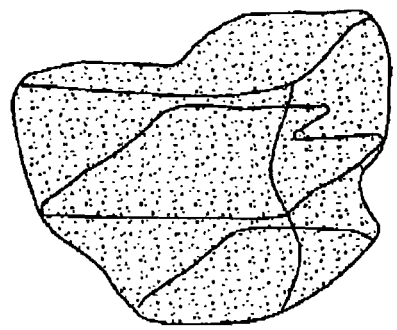
FIGS. 16A through 16C are illustrations of an embodiment of the present invention for 3D dose volume painting.
Figure 16B:
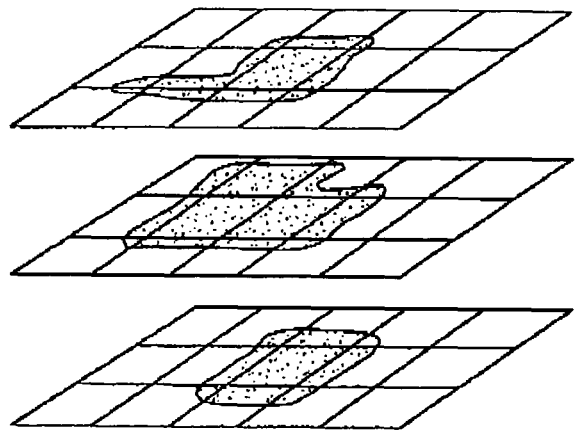
Figure 16C:
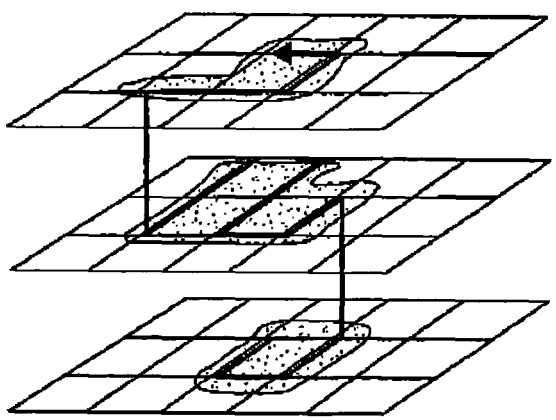

FIG. 16 shows an example of an embodiment of the present invention for 3D dose volume painting solutions as described herein. The first step, shown in FIG. 16A is to impose a 3D grid structure to the given 3D target volume. FIG. 16B shows an example of a possible 3D grid structure (vertical edges omitted) imposed on the tumor volume in FIG. 16A. Next, 3D grid shifting is applied to minimize set S of intersections that have to be traversed by the paintbrush route. This is a similar adjustment of the set S as described above in the 2D dose painting algorithm. Finally, a traveling salesman tour of the optimal set of intersections will yield the desired paintbrush tour as shown in FIG. 16C.

The invention claimed is:

1. A system for developing a dynamic radiosurgery plan to eradicate a tumor volume located in any anatomical site other than the breast area using dose volume painting and an optimal path of travel, such that each point of the tumor volume is covered by the dose volume during the path of travel, the system comprising a Gamma Knife radiation delivery system, a microprocessor, a memory and a program, said program residing in said memory and said microprocessor being configured to execute the program, said program comprising a planning algorithm, wherein said planning algorithm comprises the steps of:
  (a) imposing a 3D grid structure underlying the tumor volume to obtain an underlying grid structure;
  (b) determining a set of intersections on the underlying grid structure that must be traversed by dose shots to cover the tumor volume;
  (c) shifting the underlying grid structure to minimize the set of intersections to improve quality and duration of a final route of the dynamic radiosurgery plan;
  (d) generating an initial set of potential dose shots;
  (e) optimizing the initial set of potential dose shots and selecting a subset of dose shots;
  (f) calculating a path for the locations of the subset of dose shots;
  (g) producing the dynamic radiosurgery plan based on the path for the locations of the subset of dose shots; and (h) performing a final dose calculation on the path using fine interpolations.

2. The system for developing a dynamic radiosurgery plan to eradicate a tumor volume of claim 1, wherein the path for locations of the subset of dose shots is a two-dimensional path.

3. The system for developing a dynamic radiosurgery plan to eradicate a tumor volume of claim 1, wherein the path for locations of the subset of dose shots is a three-dimensional path.

4. The system for developing a dynamic radiosurgery plan to eradicate a tumor volume of claim 1, wherein one or more dose shots of the subset of dose shots are high dose shots.

5. The system for developing a dynamic radiosurgery plan to eradicate a tumor volume of claim 1, wherein one or more dose shots of the subset of dose shots are low dose shots.

6. The system for developing a dynamic radiosurgery plan to eradicate a tumor volume of claim 1, wherein said shifting step further comprises the step of rotating the underlying grid structure to further minimize the set of intersections.

7. The system for developing a dynamic radiosurgery plan to eradicate a tumor volume of claim 1, wherein one or more dose shots of the subset of dose shots are randomly scattered to cover the tumor volume.

8. The system for developing a dynamic radiosurgery plan to eradicate a tumor volume of claim 1, wherein the calculating a path for the locations of the subset of high dose shots is a final radiosurgery plan.

9. The system for developing a dynamic radiosurgery plan to eradicate a tumor volume of claim 1, wherein the Gamma Knife radiation delivery system includes a beam focal spot, said beam focal spot remains in a fixed location, and said tumor volume is moved in relation to said fixed beam focal spot.

10. The system for developing a dynamic radiosurgery plan to eradicate a tumor volume of claim 9, wherein said tumor volume is moved in relation to said beam focal spot at a constant speed.

11. The system for developing a dynamic radiosurgery plan to eradicate a tumor volume of claim 9, wherein said tumor volume is moved in relation to said beam focal spot at a varying speed, thereby increasing the dose volume at locations of the tumor volume.

12. The system for developing a dynamic radiosurgery plan to eradicate a tumor volume of claim 1, wherein a dose volume gradient between the tumor volume and a surrounding critical structure is increased based on said planning algorithm.

13. The system for developing a dynamic radiosurgery plan to eradicate a tumor volume of claim 1, wherein said planning algorithm is fully automatic.

14. A method for eradicating a tumor volume located in any anatomical site other than the breast area using dose volume painting and an optimal path of travel, such that each point of the tumor volume is covered by the dose volume during the path of travel, comprising the steps of:
(a) imposing a 3D grid structure underlying the tumor volume to obtain an underlying grid structure.
(b) determining a set of intersections on the underlying grid structure that must be traversed by dose shots to cover the tumor volume;
(c) shifting the underlying grid structure to minimize the set of intersections to improve quality and duration of a final route of the dynamic radiosurgery plan;
(d) generating an initial set of potential dose shots;
(e) optimizing the initial set of potential dose shots and selecting a subset of dose shots;
(f) calculating a path for the locations of the subset of dose shots;
(g) producing a radiosurgery plan based on the path for the locations of the subset of dose shots;
(h) performing a final dose calculation on the path using fine interpolations; and
(i) using a Gamma Knife radiation system to cover each point of the tumor volume based on the final dose calculation.

15. The method for developing a dynamic radiosurgery plan to eradicate a tumor volume of claim 14, wherein the path for locations of the subset of dose shots is a two-dimensional path.

16. The method for developing a dynamic radiosurgery plan to eradicate a tumor volume of claim 14, wherein the path for locations of the subset of dose shots is a three-dimensional path.

17. The method for developing a dynamic radiosurgery plan to eradicate a tumor volume of claim 14, wherein one or more dose shots of the subset of dose shots are high dose shots.

18. The method for developing a dynamic radiosurgery plan to eradicate a tumor volume of claim 14, wherein one or more dose shots of the subset of dose shots are low dose shots.

19. The method for developing a dynamic radiosurgery plan to eradicate a tumor volume of claim 14, further comprising the step of rotating the underlying grid structure to further minimize the set of intersections.

20. The method for developing a dynamic radiosurgery plan to eradicate a tumor volume of claim 14, wherein one or more dose shots of the subset of dose shots are randomly scattered to cover the tumor volume.

21. The method for developing a dynamic radiosurgery plan to eradicate a tumor volume of claim 14, wherein the calculating a path for the locations of the subset of high dose shots is a final radiosurgery plan.

22. The method for developing a dynamic radiosurgery plan to eradicate a tumor volume of claim 14, wherein the Gamma Knife radiation delivery system includes a beam focal spot, said beam focal spot remains in a fixed location, and said tumor volume is moved in relation to said fixed beam focal spot.

23. The method for developing a dynamic radiosurgery plan to eradicate a tumor volume of claim 22, wherein said tumor volume is moved in relation to said beam focal spot at a constant speed.

24. The method for developing a dynamic radiosurgery plan to eradicate a tumor volume of claim 22, wherein said tumor volume is moved in relation to said beam focal spot at a varying speed, thereby increasing the dose volume at locations of the tumor volume.

25. The method for developing a dynamic radiosurgery plan to eradicate a tumor volume of claim 14, wherein a dose volume gradient between the tumor volume and a surrounding critical structure is increased.

26. The method for developing a dynamic radiosurgery plan to eradicate a tumor volume of claim 14, wherein step (a) through step (i) are performed automatically.

27. A method for developing a dynamic radiosurgery plan to eradicate a tumor volume located in a brain area using dose volume painting and an optimal path of travel, such that each point of the tumor volume is covered by the dose volume during the path of travel, the method utilizing a Gamma Knife radiation delivery system, a microprocessor, a memory and a program, said program residing in said memory and said microprocessor being configured to execute the program, said program comprising a planning algorithm, wherein said planning algorithm comprises the steps of:
- (a) imposing a 3D lattice structure to the tumor volume located in the brain area;
- (b) determining a set of intersections on the 3D lattice structure that must be traversed by one or more dose shots to cover the tumor volume located in the brain area;
- (c) minimizing the set of intersections on the 3D lattice structure that must be traversed by the one or more dose shots to improve quality and duration of a final route of the dynamic radiosurgery plan by performing one or both of the following: shifting the 3D lattice structure and rotating the 3D lattice structure;
- (d) generating an initial set of potential dose shots;
- (e) optimizing the initial set of potential dose shots;
- (f) selecting a subset of dose shots from the initial set of potential dose shots;
- (g) calculating a path for the locations of the subset of dose shots;
- (h) producing the dynamic radiosurgery plan based on the path for the locations of the subset of dose shots;
- (i) performing a final dose calculation on the path using fine interpolations; and
- (j) using the Gamma Knife radiation delivery system on the tumor volume located in the brain area.

* * * * *